United States Patent [19]
Shani et al.

[11] Patent Number: 5,348,545
[45] Date of Patent: Sep. 20, 1994

[54] GUIDING CATHETER FOR THE RIGHT CORONARY ARTERY

[75] Inventors: Jacob Shani, Brooklyn, N.Y.; Gurpal Paintal; Bruce Wand, both of San Jose, Calif.

[73] Assignee: Advanced Cardiovascular Systems, Inc., Santa Clara, Calif.

[21] Appl. No.: 742,216

[22] Filed: Aug. 6, 1991

Related U.S. Application Data

[63] Continuation of Ser. No. 571,079, Aug. 21, 1990, abandoned.

[51] Int. Cl.$^5$ ............................................. A61M 25/00
[52] U.S. Cl. ..................................... 604/281; 604/280
[58] Field of Search .............................. 604/280-283, 604/264, 95; 128/772, 656-658

[56] References Cited

U.S. PATENT DOCUMENTS

| | | | |
|---|---|---|---|
| 1,060,665 | 5/1913 | Bell . | |
| 3,938,501 | 2/1976 | Erikson | 604/281 |
| 4,033,331 | 7/1977 | Guss et al. | 604/281 |
| 4,117,835 | 10/1978 | Erikson | 604/280 |
| 4,292,976 | 10/1981 | Banka | 128/656 |
| 4,323,071 | 4/1982 | Simpson et al. | 604/98 |
| 4,430,083 | 2/1984 | Ganz et al. | 604/283 |
| 4,547,193 | 10/1985 | Rydell | 604/282 |
| 4,563,181 | 1/1986 | Wijayarathna et al. | 128/2.05 |
| 4,569,347 | 2/1986 | Frisbie | 604/164 |
| 4,636,346 | 1/1987 | Gold et al. . | |
| 4,664,657 | 5/1987 | Williamitis et al. | 604/265 |
| 4,747,840 | 5/1988 | Ladika et al. | 604/281 |
| 4,863,442 | 9/1989 | De Mello et al. | 604/282 |
| 4,882,777 | 11/1989 | Narula | 604/281 |
| 4,883,058 | 11/1989 | Ruiz | 604/281 |
| 4,886,506 | 12/1989 | Lavgren et al. | 604/282 |
| 4,935,017 | 6/1990 | Sylvanowicz | 604/281 |
| 4,961,731 | 10/1990 | Bodicky et al. | 604/281 |
| 4,968,307 | 11/1990 | Dake et al. | 604/280 |
| 4,973,306 | 11/1990 | Ruiz | 128/658 |
| 5,016,640 | 5/1991 | Ruiz | 128/658 |
| 5,044,369 | 9/1991 | Sahota | 128/658 |
| 5,069,673 | 12/1991 | Shwab | 604/281 |
| 5,188,619 | 2/1993 | Myers | 604/280 |

*Primary Examiner*—C. Fred Rosenbaum
*Assistant Examiner*—Mark Bockelman
*Attorney, Agent, or Firm*—Crosby, Heafey, Roach & May

[57] ABSTRACT

A guiding catheter for disposition within a patient's right coronary artery having a main tubular section which is relatively straight, a second curved tubular section immediately distal to the main tubular section and much shorter than the main tubular section which curves away from the longitudinal axis of the main tubular section, a third tubular section which is relatively straight and distally adjacent to the second tubular section and a fourth tubular section on the distal end of the catheter which curves toward the longitudinal axis of the main tubular section. The radius of curvature of the second tubular section is much greater than the radius of curvature of the fourth tubular section. A line tangent to the second curved section intersects an extension of the longitudinal axis of the main tubular section at a minimum obtuse angle greater than 100°.

The catheter can be advanced through a patient's aorta and easily seated into the right coronary ostium thereof. The distal tip of the catheter is preferentially oriented toward the outer curvature of the aorta, so it needs little or no torquing to be guided into the right coronary ostium. Moreover, with the main catheter body wedged up against the upper inner surface of the aortic arch there is little tendency for the distal end of the catheter to back out of the ostium during an angioplasty procedure. A balloon dilatation catheter is advanced through the inner lumen of the guiding catheter.

10 Claims, 1 Drawing Sheet

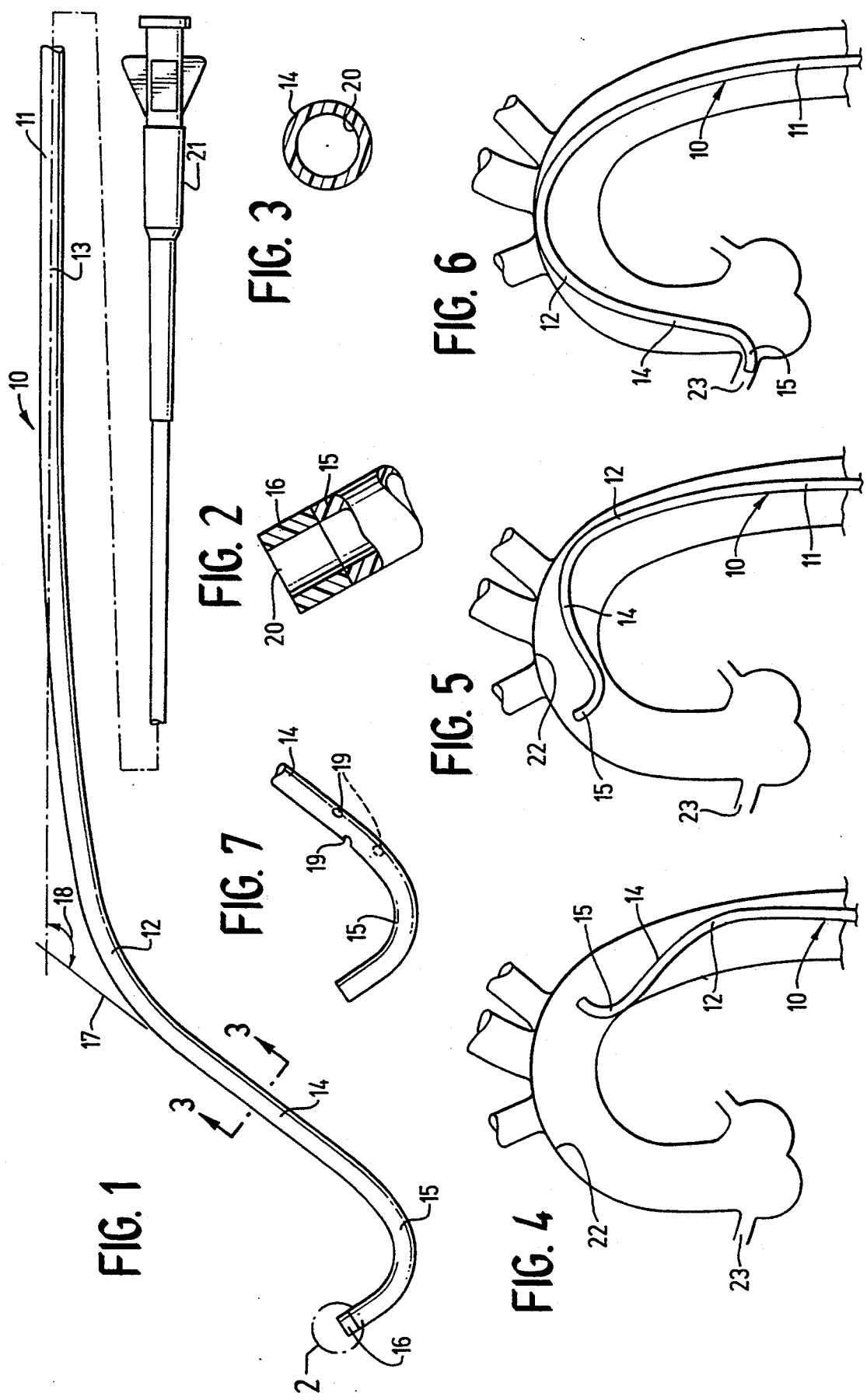

GUIDING CATHETER FOR THE RIGHT CORONARY ARTERY

This a continuation of the application Ser. No. 07/571,079 which was filed on Aug. 21, 1990 now abandoned.

BACKGROUND OF INVENTION

This invention generally relates to intravascular catheters which are adapted for right coronary artery use and, more specifically, to guiding catheters for guiding dilatation catheters and the like into a patient's right coronary artery in procedures such as percutaneous transluminal coronary angioplasty (PTCA).

In the classic PTCA procedure, a guiding catheter having a preformed distal tip is percutaneously introduced into the cardiovascular system of a patient and advanced therein until the distal tip thereof is in the ostium of the desired coronary artery. A guidewire and a dilatation catheter having a balloon on the distal end thereof are introduced into and advanced through the guiding catheter to the distal tip thereof, with the guidewire slidably disposed within an inner lumen of the dilatation catheter. The guidewire is first advanced out the distal tip of the guiding catheter into the patient's coronary vasculature until the distal end of the guidewire crosses the lesion to be dilated, then the dilation catheter is advanced over the previously advanced guidewire until the dilatation balloon is properly positioned across the lesion. Once properly positioned, the balloon is inflated to a predetermined size with radiopaque liquid at relatively high pressures (e.g., generally 4–12 atmospheres) to dilate the lumen of the diseased artery. The balloon is then deflated so that the dilatation catheter can be removed and blood flow resumed through the dilated artery.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,582,185 (Samson); U.S. Pat. No. 4,616,652 (Simpson); and U.S. Pat. No. 4,638,805 (Powell) which are hereby incorporated herein in their entirety by reference thereto.

Typically, a right Judkins guiding catheter is employed when performing a PTCA in a right coronary artery. A guiding catheter with an Amplatz curve can be used, but such a catheter is used with less frequency because it can cause injury to the coronary artery ostium if it is removed too quickly. The right Judkins catheter generally has three curves in the distal end, primary curve at the very distal tip, a much larger radiused secondary curve about 4–6 cm proximal from the primary curve and a tertiary curve proximal to the secondary curve having a much larger radius of curvature than the secondary curve. For a detailed description of the right Judkins guiding catheter, reference is made to *RADIOLOGICAL CLINICS OF NORTH AMERICA* Vol. VI, No. 3 December 1968 which is incorporated herein by reference.

However, the distal tip of the right Judkins catheter can be difficult to place within the ostium of the right coronary artery and once properly placed in the ostium thereof the distal tip can be easily displaced therefrom during angioplasty and other coronary vascular procedures. For example, the distal tip can back out of the ostium and interfere with proper placement of dilatation catheters into the coronary anatomy.

Many guiding catheters used in angioplasty procedures have perfusion ports a short distance proximal to the distal end so that, when the distal tip is seated within the coronary ostium, blood within the aorta will perfuse through the ports into the inner lumen of the guiding catheter and out the axial opening in the distal tip. However, when radiopaque dye is injected through the guiding catheter from the proximal end thereof, much of the dye is ejected out through the perfusion ports into the aorta. Because of the loss of dye into the aorta, insufficient dye will be introduced into the coronary arteries through the distal tip of the guiding catheter which makes fluoroscopic observation of the catheter very difficult.

What has been needed and heretofore unavailable is a guiding catheter which is easily positioned within the patient's right coronary artery and which provides sufficient distal push to the distal end of the catheter to ensure its placement within the ostium during vascular procedures. Additionally, there is also a need for a guiding catheter having perfusion ports in the distal end which minimize the ejection of radiopaque dye into the aorta without loss of blood perfusion characteristics. The catheter designs of the present invention satisfy these needs.

SUMMARY OF THE INVENTION

The present invention is directed to a torquable guiding catheter which facilitates the placement of the distal tip of the catheter within the ostium of the patient's right coronary artery and which urges the distal tip into the ostium so that it is maintained therein during a coronary vascular procedure.

The catheter of the invention generally includes an elongated, torqueable catheter body comprising an elongated relatively straight main tubular section, a second tubular section, distal to the main section which is much shorter than the main section and which curves away from the longitudinal axis of the main section and a third relatively straight tubular section distal to the second tubular section and a fourth curved tubular section distal to the third tubular section which is much shorter than the second section and which curves toward the longitudinal axis of the main section. The distal tip of the fourth section is spaced from an extension of the longitudinal axis of the main section.

The curvature of the second section is such that any tangent line thereto is at a minimum angle of between about 100° and 160°, preferably 115°–135°, from an extension of the longitudinal axis of the main tubular section. The overall length of the catheter is about 80 to about 120 cm. The second section is about 5 to about 20 cm in length, and the third and fourth sections are about 3 cm to about 10 cm in length. Preferably the distal end of the fourth section is spaced about 3 to about 15 cm, preferably about 5 to about 10 cm from the extension of the longitudinal axis.

The distal tip of the fourth catheter section, is provided with at least three perfusion ports generally equally (radially) spaced about the periphery of the catheter e.g. about 120° from each other and preferably longitudinally spaced from each other to form a spiral arrangement. The perfusion ports are disposed a sufficient distance from the distal end of the catheter so that they remain within the aorta when the distal end is seated in the ostium. Preferably, the most distal perfusion port is about 2 to about 6 cm from the distal tip. The remaining perfusion ports are sequentially disposed about 0.1 to about 1 cm, preferably about 0.2 to about 0.7 cm (measured longitudinally along the axis), from the preceding port. The port diameter can range from about 0.03 to about 0.04 inch (0.76–1.02 mm), and is typically about 0.035 inch (0.89 mm).

When the catheter of the invention is advanced through a patient's aorta, the distal tip preferentially orients toward the outer portion of the aorta. This preferential orientation greatly simplifies the use of the catheter, because as a result of this tendency for a specific orientation very little torquing of the catheter from the proximal end thereof is necessary to position the distal tip within the right coronary ostium. The orientation of the distal tip of the catheter when adjacent the right coronary ostium is usually less than about 90° from the ostium. This is to be compared with a right Judkins catheter wherein the distal tip is typically oriented about 180° from the right coronary ostium and requires considerable torquing to turn the curved distal tip so that it can be inserted into the ostium in the right direction. Once the distal tip of the catheter of the invention is advanced into the right coronary ostium and the main tubular section is wedged up against the upper inner surface of the aortic arch, there is sufficient pressure or force against the distal tip of the catheter to ensure that it remains seated within the ostium during angioplasty, or other vascular procedures.

These and other advantages of the invention will become more apparent from the following detailed description thereof when taken in conjunction with the attached accompanying drawings.

BRIEF DESCRIPTION OF THE DRAWINGS

FIG. 1 is an elevational view of a guiding catheter embodying features of the invention.

FIG. 2 is a transverse cross sectional view taken along the lines 2—2 shown in FIG. 1.

FIG. 3 is an enlarged view partially in section of the distal tip of the catheter held in FIG. 1.

FIGS. 4–6 schematically illustrate the advancement of the distal tip of the catheter shown in FIG. 1 through a patient's aorta into the right coronary ostium.

FIG. 7 is an elevation view of the distal tip of the catheter provided with perfusion ports therein.

DETAILED DESCRIPTION OF THE INVENTION

FIGS. 1–3 illustrate a guiding catheter 10 embodying features of the invention. The catheter 10 has a relatively straight main tubular section 11, a second tubular section 12 distally adjacent to the main tubular section 11 and which curves away from the longitudinal axis 13 thereof, a third, relatively straight tubular section 14 distally adjacent to the second tubular section and a fourth section 15 at the distal end of the catheter 10 which curves toward the extension of the longitudinal axis 13. As shown in FIG. 3, the distal end of the catheter 10 may be provided with a soft flexible tip 16 to avoid traumatic engagement with walls of the aorta or artery or tissue about the right coronary ostium when the catheter is advanced through a patient's vascular system.

The second tubular section curves away from the longitudinal axis 13 so that a tangent line 17 thereto intersects the extension of the longitudinal axis at a minimum obtuse angle 18 between about 100° and 165°, preferably about 115° and about 135°. A minimum obtuse angle will generally be measured at the distal end of the second curved section 12 and is usually at the same angle as the longitudinal axis of the fourth straight tubular section 14. The radius of curvature of the second tubular section 13 is much larger than the radius of curvature of the fourth, most distal section 15 of the catheter.

The fourth tubular section 15 is provided with perfusion ports 19 which are spirally arranged in the wall of the tubular section. The most distal port is spaced about 3.5 cm from the distal tip, the second about 4.0 cm and the third about 4.3 cm to ensure that these ports remain in the aorta when the distal tip is seated in the coronary ostium. With this arrangement there is little loss of radiopaque dye when it is injected into the inner lumen 20 of the catheter 10 from the proximal end thereof and there is adequate blood perfusion through the inner lumen 19 into the patient's coronary artery.

The proximal end of the catheter 10 is provided with an adapter 21 to facilitate the introduction into the inner lumen 19 of radiopaque fluid and various types of catheters such as a dilatation catheter 22 as shown in FIG. 1 or an atherectomy catheter.

When using the catheter 10 of the invention, it is first percutaneously introduced into a patient's right femoral artery by way of a conventional Seldinger technique. The catheter 10 is then advanced through the right femoral and iliac arteries, the abdominal aorta and the aortic arch 22. As shown in FIGS. 4–6, the distal curved section 14 is oriented generally toward the exterior curve of the aortic arch 22 as it is advanced therein so that when the distal end of the catheter is in the vicinity of the right coronary ostium 23, the catheter 10 needs little torquing from the proximal end thereof in order for this distal curved section 14 to be properly seated within the right coronary ostium 23. Once properly seated, the main tubular section 11 of the catheter 10 is advanced further so that it becomes wedged up against the upper inner surface of the aortic arch 22 to thereby ensure that the distal curved section 14 does not back out of the ostium during the use, such as when advancing a dilatation catheter into the patient's coronary artery.

Once the guiding catheter is properly positioned within the patient's vascular system, with the distal end thereof seated within the ostium of the right coronary artery, a balloon dilatation catheter(not shown) can be introduced into the proximal end of the guiding catheter and be advanced therein until the distal end of the dilatation catheter extends out of the distal end of the guiding catheter. The balloon on the distal end of the dilatation catheter can then be inflated to dilate a stenosis within the patient's coronary artery. After the dilation, the balloon can be deflated and the dilatation catheter can be removed from the guiding catheter.

The inner and outer diameters of the guiding catheter 10 will generally have essentially the same dimensions as conventional guiding catheters. The O.D. may range from about 2 to 12 french (1.65–3.96 mm), preferably about 7 to about 9 french (2.31–2.92 mm). Typically the outer diameter is about 8 french (2.64 mm) and the inner diameter is about 6 french (2 mm).

The catheter 10 is torqueable as with conventional guiding catheters to enable the distal curved section 14 to be guided into the right coronary ostium 23 by rotating the proximal end of the catheter 10. A conventional guiding catheter construction can be employed to provide suitable torquing characteristics. Most guiding catheters are of a composite structure with a high strength fiber (e.g., stainless steel, aramid, nylon and the like) braided or wrapped and impregnated with suitable plastic such as polyurethane or an epoxy. The inner lumen is usually provided with lubricous coating or layer, e.g. polytetrafluorethylene sold under the trademark TEFLON by Dupont. Preferably the outside of catheter 10 is covered with a plastic jacket in order to provide a smooth surface.

While the invention has been described herein in terms of a guiding catheter for use in angioplasty in the right coronary artery, the three perfusion ports may be provided in the distal ends of guiding catheters which have other shapes and which are designed for other uses in other arteries. Other modifications and improvements can be made to the present invention without departing from the scope thereof.

What is claimed is:

1. A torqueable guiding catheter adapted to guide a dilatation catheter in a patient's right coronary artery which has an elongated catheter body with an inner lumen having a lubricous coating thereon extending along essentially the entire length of the guiding catheter, the catheter body comprising:
   a) a main, essentially straight tubular section having a proximal end which provides access to the inner lumen therein;
   b) a second tubular section which is distal and adjacent to the main section, which is much shorter than the main tubular section and which is preformed so as to curve away from an extension of the longitudinal axis of the main tubular section;
   c) a third relatively straight tubular section which is distal and adjacent to the second tubular section and which forms an included angle with the extension of the longitudinal axis of the main tubular section from 100° to 160° so that the main tubular section and the third tubular section form an obtuse angle;
   d) a fourth tubular section which is distal and adjacent to the third tubular section, which is much shorter than the second tubular section and which is preformed so as to have a smaller radius of curvature than the second tubular section and to curve toward and to have a distal end spaced 3 to 15 cm from the extension of the longitudinal axis of the main tubular section; and
   e) at least three perfusion ports in the fourth tubular section having diameter of about 0.03 to about 0.04 inch, with the most distal perfusion port being spaced between 2 cm to 6 cm from the distal end of the fourth tubular section and the individual perfusion ports being spaced 0.1 to about 1 cm from each other.

2. The torqueable guiding catheter of claim 1 wherein the included obtuse angle between the extension of the longitudinal axis of the main tubular section and the third tubular section is between about 115° and about 135°.

3. The torqueable guiding catheter of claim 1 wherein the distal tip thereof is formed from a relatively soft elastomeric material to avoid traumatic engagement thereof with tissue during the use thereof.

4. The torqueable guiding catheter of claim 1 wherein the fourth tubular section has a distal tip which is spaced about 3 to about 10 cm from the extension of the longitudinal axis of the main tubular member.

5. The torqueable guiding catheter of claim 1 wherein the fourth tubular section has a distal tip which is spaced about 5 to about 10 cm from the extension of the longitudinal axis of the main tubular member.

6. The torqueable guiding catheter of claim 1 wherein the perfusion ports are equally spaced from one another about the longitudinal axis of the fourth tubular section.

7. The torqueable guiding catheter of claim 1 wherein the perfusion ports are longitudinally spaced from each other a distance of about 0.2 to about 0.07 cm.

8. A torquable guiding catheter for guiding an intravascular catheter to a patient's right coronary artery comprising an elongated tubular member having proximal essentially straight portion with a proximal end and a distal portion which deviates away from the proximal straight portion with an included angle therebetween of 100° to 160° so that the essentially straight portion and the distal portion form an obtuse angle and with a distal end which is curved toward an extension of a longitudinal axis of the proximal straight portion and dimensioned to be easily seated within the ostium of the patient's right coronary artery, an inner lumen extending the length thereof from the distal to the proximal end and at least three perfusion ports in the curved distal portion having diameter of about 0.03 to about 0.04 inch which are equally spaced radially from each other, which are in fluid communication with the inner lumen and the most distal perfusion port being spaced longitudinally between 2 cm to 6 cm from a distal end of the distal portion and the individual perfusion ports being longitudinally spaced 0.1 to about 1 cm from each other.

9. The guiding catheter of claim 8 wherein the catheter has a distal end which is curved and dimensioned so as to be easily seated within the ostium of the patient's right coronary artery and wherein perfusion ports are provided in the distal portion spaced a sufficient distance from the distal end so that when the distal end is seated within a patient's coronary ostium perfusion ports are disposed within the patient's ascending aorta adjacent the ostium.

10. The torquable guiding catheter of claim 9 wherein the perfusion ports have diameters of about 0.035 inch.

* * * * *

UNITED STATES PATENT AND TRADEMARK OFFICE
CERTIFICATE OF CORRECTION

PATENT NO. : 5,348,545

DATED : September 20, 1994

INVENTOR(S) : Jacob Shani et al.

It is certified that error appears in the above-identified patent and that said Letters Patent is hereby corrected as shown below:

In col. 5, line 52, "diameter" should be --diameters--.

In col. 5, line 56, "about" should be deleted.

Signed and Sealed this

Twenty-eight Day of March, 1995

Attest:

BRUCE LEHMAN

Attesting Officer     Commissioner of Patents and Trademarks